(12) United States Patent
Shibuya et al.

(10) Patent No.: US 7,561,974 B2
(45) Date of Patent: Jul. 14, 2009

(54) SYSTEM AND METHOD FOR IDENTIFYING GENES

(75) Inventors: Tetsuo Shibuya, Yamato (JP); Isidore Rigoutsos, Astoria, NY (US)

(73) Assignee: International Business Machines Corporation, Armonk, NY (US)

( * ) Notice: Subject to any disclaimer, the term of this patent is extended or adjusted under 35 U.S.C. 154(b) by 152 days.

(21) Appl. No.: 10/059,421

(22) Filed: Jan. 31, 2002

(65) Prior Publication Data

US 2002/0173918 A1 Nov. 21, 2002

Related U.S. Application Data

(60) Provisional application No. 60/265,553, filed on Feb. 1, 2001.

(51) Int. Cl.
*G01N 33/48* (2006.01)
(52) U.S. Cl. ..................................................... 702/20
(58) Field of Classification Search .................. 702/19, 702/20
See application file for complete search history.

(56) References Cited

U.S. PATENT DOCUMENTS 5,966,712 A 10/1999 Sabatini et al.

OTHER PUBLICATIONS

Benson et al., Nucleic Acids Research, 1997, vol. 25, pp. 1-6.*
Rigoutsos et al., Bioinformatics, vol. 14, pp. 55-67, 1998.*
Bairoch et al., Nucleic Acids Research, vol. 25, No. 1, pp. 217-221, 1997.*
Nishikawa et al., Genome Informatics, vol. 11, pp. 12-23, 2000.*
Baxevanis et al., Bioinformatics, Second Edition, John Wiley & Sons, Inc., pp. 202-203, 2001.*
Altschul et al., J. Mol. Biol., vol. 215, pp. 403-410, 1990.*
Rigoutsos et al., Proc Inf Conf Intell Syst Mol Biol., 1999; pp. 223-233.*
Delcher et al., Nucleic Acids Research, 1999, vol. 27, pp. 4636-4641.*
Ganguly et al., Comput. Biol. Med., vol. 26, No. 3, pp. 199-207, 1996.*
Floratos et al., RECOMB '99, Lyon France, 1999, pp. 164-173.*
Ishikawa et al., FEMS Microbiology Letters, 174, pp. 251-253, 1999.*

* cited by examiner

*Primary Examiner*—Cheyne D Ly
(74) *Attorney, Agent, or Firm*—Vazken Alexanian; McGinn IP Law Group, PLLC

(57) ABSTRACT

A system and method for identifying genes that employs a pattern database, an input device for inputting a DNA sequence, and a processor for processing the DNA sequence and patterns to identify a putative gene. The processor may determine open reading frames (ORFs) in the DNA sequence, generate an amino acid translation for each ORF, and identify a match of a pattern in the amino acid translation.

30 Claims, 5 Drawing Sheets

| # | ORGANISM | ABBR. | LENGTH | #ORF | #CDS |
|---|---|---|---|---|---|
| 1 | ARCHAEOGLOBUS FULGIDUS DSM4304 | AF | 2,178,400 | 73,238 | 2,407 |
| 2 | METHANOCOCCUS JANNASCHII DSM2611 | MJ | 1,664,970 | 74,456 | 1,715 |
| 3 | METHANOBACTERIUM THERMOAUTOTROPHICUM DELTA H | MT | 1,751,377 | 64,726 | 1,869 |
| 4 | PYROCOCCUS ABYSSI GE5 | PA | 1,765,118 | 64,436 | 1,765 |
| 5 | AQUIFEX AEOLICUS VF5 | AA | 1,551,335 | 50,591 | 1,523 |
| 6 | BORRELIA BURGDORFERI B31 | BB | 910,724 | 40,403 | 850 |
| 7 | BACILLUS SUBTILIS 168 | BS | 4,214,814 | 167,735 | 4,101 |
| 8 | CAMPYLOBACTER JEJUNI NCTC11168 | CJ | 1,641,481 | 72,016 | 1,635 |
| 9 | CHLAMYDIA PNEUMONIAE CWL029 | CPc | 1,230,230 | 50,872 | 1,052 |
| 10 | CHLAMYDIA PNEUMONIAE AR39 | CPa | 1,229,853 | 50,840 | 1,110 |
| 11 | CHLAMYDIA TRACHOMATIS SEROVAR D | CT | 1,042,519 | 42,338 | 894 |
| 12 | ESCHERICHIA COLI K12-MG1655 | EC | 4,639,221 | 163,600 | 4,285 |
| 13 | HAEMOPHILUS INFLUENZAE KW20 | HI | 1,830,138 | 83,944 | 1,709 |
| 14 | HELICOBACTER PYLORI 26695 | HP | 1,667,867 | 67,227 | 1,567 |
| 15 | RICKETTSIA PROWAZEKII MADRID E | RP | 1,111,523 | 53,656 | 835 |
| 16 | SYNECHOCYSTIS SP. PCC6803 | SS | 3,573,470 | 141,204 | 3,182 |
| 17 | THERMOTOGA MARITIMA MSB8 | TM | 1,860,725 | 57,584 | 1,846 |

TABLE 1. DETAILS ON THE 17 GENOMES USED IN OUR EXPERIMENTS

FIG.4A

|  | (a) 1.0 × #CDS | | | | (B) 1.1 × #CDS | | | |
| --- | --- | --- | --- | --- | --- | --- | --- | --- |
|  | ANNOTATED | | ADDITIONAL HITS | SCORE | ANNOTATED | | ADDITIONAL HITS | SCORE |
| AF | 2319 | 96.3 | 88 | 41 | 272.0 | 2381 | 98.9 | 267 | 55 | 103.7 |
| MJ | 1689 | 98.5 | 26 | 7 | 148.6 | 1715 | 100.0 | 172 | 12 | 18.0 |
| MT | 1816 | 97.2 | 53 | 6 | 166.2 | 1853 | 99.1 | 203 | 9 | 79.2 |
| PA | 1742 | 98.7 | 23 | 5 | 188.7 | 1765 | 100.0 | 177 | 20 | 9.7 |
| AA | 1491 | 97.9 | 32 | 6 | 418.3 | 1520 | 99.8 | 156 | 25 | 69.2 |
| BB | 850 | 100.0 | 0 | 0 | 18.0 | 850 | 100.0 | 86 | 0 | 0.8 |
| BS | 3959 | 96.5 | 143 | 15 | 214.9 | 4043 | 98.6 | 470 | 39 | 108.0 |
| CJ | 1630 | 99.7 | 5 | 0 | 9.2 | 1634 | 99.9 | 165 | 0 | 0.7 |
| CPc | 1050 | 99.8 | 2 | 1 | 48.5 | 1052 | 100.0 | 106 | 5 | 2.3 |
| CPa | 1104 | 99.5 | 6 | 3 | 13.1 | 1110 | 100.0 | 111 | 5 | 2.1 |
| CT | 892 | 99.8 | 2 | 2 | 56.4 | 893 | 99.9 | 91 | 2 | 2.4 |
| EC | 3958 | 92.4 | 327 | 24 | 595.1 | 4062 | 94.8 | 652 | 35 | 418.4 |
| HI | 1697 | 99.3 | 12 | 6 | 78.8 | 1709 | 100.0 | 171 | 31 | 10.1 |
| HP | 1552 | 99.0 | 15 | 10 | 33.7 | 1565 | 99.9 | 159 | 15 | 1.5 |
| RP | 833 | 99.9 | 1 | 1 | 76.6 | 834 | 100.0 | 84 | 2 | 1.7 |
| SS | 3001 | 94.5 | 174 | 4 | 408.4 | 3068 | 96.6 | 425 | 8 | 267.1 |
| TM | 1781 | 96.5 | 65 | 27 | 336.6 | 1813 | 98.2 | 218 | 37 | 159.6 |

TABLE 2. PREDICTION WITH OPTIMAL SEQLET WEIGHTS FOR EACH GENOME.

FIG.4B

SYSTEM AND METHOD FOR IDENTIFYING GENES

CROSS REFERENCE TO RELATED APPLICATIONS

This Application claims the benefit of Provisional Application No. 60/265,553 which was filed on Feb. 1, 2001 by Isidore Rigoutsos, et al., assigned to the present assignee, and which is incorporated herein by reference.

BACKGROUND OF THE INVENTION

1. Field of the Invention

The present invention generally relates to a system and method for identifying genes and, more particularly, a system and method which utilizes a database of patterns to identify genes.

2. Description of the Related Art

Gene identification is one of the most important problems in molecular biology and has been receiving increasing attention with the advent of automated large scale sequencing projects. Indeed, more than 70 complete genomes currently exist in the public domain, while the sequencing of many others is currently in progress. Consequently, the automated identification of the protein coding regions in a newly sequenced genome is gaining importance.

Accurate gene prediction is of relevance to many biological applications. For instance, the predicted coding regions can be used to generate probes for a DNA microarray, or to form the basis for knockout experiments. In addition, the candidate proteins that correspond to these predicted genes might be used as new drug targets, and so forth.

Specific attention has been given to the prokaryotic gene identification problem. With the exception of a handful of reported instances in archaeal organisms, splicing generally does not occur in prokaryotes and thus the problem of gene identification in these organisms is assumed to be simpler than its eukaryotic counterpart. Even so, the available schemes for the in silico gene prediction on prokaryotic genomes can be improved further and increasingly accurate prediction methods are always sought.

Over the years, a large number of methods have been proposed that address the gene identification problem. These methods can be largely divided into two categories. The first school of thought makes use of the statistics of DNA sequences to determine gene locations. It was observed early on that the nucleotide usage exhibits different statistical properties in DNA regions that code for genes than it does outside: the concept of the CpG island (e.g., see Bird, A., (1987) "CpG islands are gene markers in the vertebrate nucleus", *Trends in Genetics*, 3: 342-347) is a demonstration of such a difference in statistical behavior.

Among the gene identification methods that make use of this observation, hidden Markov models (HMMs) are probably the most popular. Specifically, HMMs are used in conventional methods such as GLIMMER (e.g., see Delcher, A. L., et al (1999), "Improved Microbial Gene identification with GLIMMER", *Nucl. Acid. Res.*, 27 (23): 4636-4641; and Salzberg, S. L., et al., (1998) "Microbial Gene Idenfication Using Interpolated Markov Models", *Nucl. Acid. Res.*, 26(2): 544-548) and GeneMark (Lukashin, A. V., and Borodovsky, M., (1998), "GeneMark.hmm: New Solutions for Gene Identification", *Nucl. Acid. Res.*, 16(4): 1107-1115).

The second school of thought advocates a strategy that is based on similarity searches in databases containing genomic information (e.g., see Badger, J. H. and Olsen, G. J., (1999), "CRITICA: Coding Region Identification Tool Invoking Comparative Analysis", *Molecular Biology and Evolution*, 16:512-524; Bafna, V., and Huson, D. H., (2000), "The Conserved Exon Method for Gene Finding", Proc. ISMB '00; Gelfand, M. S., Mironov, A. A., and Pevzner, P., (1996) "Gene Recognition Via Spliced Alignment", *Proc. Natl. Acad. Sci.USA*, 93:9061-9066; Gish, W., and States, D. J., (1993) "Idenfication of Protein Coding Regions by Database Similarity Search, *Nat. Genet.*, 3:266-272; and Robinson, K., Gilbert., W., and Church, G., (1994) "Large-scale Bacterial Gene Discovery by Similarity Search", *Nat. Genet.*, 7:205-214). Here one searches in existing databases for either proteins or DNA regions in other genomes that share similarities with candidate proteins corresponding to open reading frames (ORFs) identified in the genome under consideration (e.g., see Burge, C., and Karlin, S., (1998), "Finding the Genes in Genomic DNA", *Current Opinion in Structural Biology*, 8:346-354; Burset, M. and Buigo, R., (1996) "Evaluation of Gene Structure Prediction Programs", *Genomics*, 34:353-367; Claverie, J. M., (1998), "Computational Methods for Exon Detection", *Molecular Biotechnology*, 10:27-48; Claverie, J. M., (1997), "Computational Methods for the Identification of Genes in Vertebrate Genomic Sequences", *Human Molecular Genetics*, 6(10):1735-1744; Fickett, J. W., (1996), "The Gene Identification Problem: An Overview for Developers", *Computers Chem.*, 20(1):103-118; and Fickett, J. W. and Hatzigeorgiou, A. G., (1997), "Eukaryotic Promoter Recognition", *Genome Research*, 7: 871-878).

However, these conventional strategies have shortcomings. Statistical methods like HMMs can find regions whose statistical behavior is similar to that of the used training set. But if no appropriate training sets are available, one must resort to using training sets that are derived through database search, or simply assume very long open reading frames to be coding for genes. The statistics of coding regions often differ from organism to organism, and ideally one ought to use HMMs whose parameters are organism-dependent if one wishes to achieve high prediction ratio. That is, one must train HMMs separately for each genome.

It has also been demonstrated that there exist many genes that are statistically distinct from other genes of the same organism, such as genes that are the result of horizontal transfer (e.g., see Kehoe, M. A., Kapur, V., et al., (1996) "Horizontal Gene Transfer Among Group A Streptococci: Implications for Pathogenesis and Epidemiology", *Trends Microbiol.*, 4(11):436-443; and Nielsen, K. M., bones, A. M., et al., (1998), "Horizontal Gene Transfer From Transgenic Plants to Terrestrial Bacteria—A Rare Event?", *FEMS Microbiol Rev.*, 22(2):79-103). Such cases typically pose challenges to statistical methods.

Finally, short genes (e.g. fewer than 60-80 a.a.) cannot be predicted easily using statistical methods. Similarity-based methods are more successful in finding short genes or genes that are statistically different from those in the rest of the organism under consideration as long as similar genes or proteins already appear in the databases being searched. Additional problems arise if the shared similarity between a candidate gene and its database counterpart is very low. On the flip-side, there is no dependence of the quality of answers on the choice of training sets. Similarity-based methods generally have an improved ability in determining the correct location of genes over statistical methods, a desirable property. It is for these reasons that large genome sequencing projects often employ a combination of methods from both schools (e.g., see Fleishman, R. D., et al., (1995), "Whole-genome Random Sequencing and Assembly of Haemophilus Influenzae", *Science*, 269: 496-512).

SUMMARY OF THE INVENTION

It is, therefore, an object of the present invention to provide a structure and method for accurately and efficiently identifying genes in DNA sequences.

The present invention includes a system for identifying genes which includes a pattern database including patterns of amino acids, an input device for inputting a DNA sequence, and a processor for processing the DNA sequence and patterns to identify a putative gene. For instance, the processor may determine possible open reading frames (ORFs) in the DNA sequence, generate an amino acid translation for each ORF, and identify a match of a pattern in the amino acid translation. The inventive system may report an ORF as a putative gene when one or more pattern matches are identified in the amino acid translation. An ORF includes a portion of the DNA sequence between a start codon and a stop codon.

The patterns may be derived from a parent database of one or more proteins and/or protein fragments. Further, the patterns may be generated (e.g., by the processor) from the amino acid sequences of the proteins and protein fragments in the parent database using a predetermined algorithm, such as the Teiresias Algorithm.

The inventive system may further include a memory device for storing data and instructions to be executed by the processor, and a display device for displaying an output from the processor.

Further, each pattern may be assigned a weight (e.g., depending upon how relevant the pattern is in determining whether an ORF is a putative gene). For instance, the processor may assign a weight to a given pattern in the pattern database. In addition, an occurrence of a pattern match in said amino acid translation may be identified with the help of a predetermined algorithm (e.g., a pattern matching algorithm) used to identify matches of a pattern in the amino acid translation.

The present invention also includes an inventive method of identifying genes which includes optionally generating a set comprising patterns of amino acids, computing an open reading frame (ORF) in a DNA sequence, generating an amino acid translation for each ORF; and identifying potential matches of the patterns in the amino acid translation. The employed collection of patterns may be generated, for example, using a predetermined algorithm, such as the Teiresias algorithm to process a parent database of one or more amino acid sequences or fragments. Further, an ORF may be reported as a putative gene when one or more pattern matches are identified in said amino acid translation.

The inventive method may also include assigning a weight to each pattern depending upon how relevant the pattern is in determining whether an ORF (e.g., an ORF in which the pattern is identified) is a putative gene. The method may also include displaying or printing instances of a pattern (e.g., pattern matches) in the amino acid translation.

The present invention also includes a programmable storage medium tangibly embodying a program of machine-readable instructions executable by a digital processing apparatus to perform the inventive method for identifying genes.

With its unique and novel features, the present invention provides a novel system and method which accurately and efficiently identifies genes. The present invention may be considered to combine the best characteristics of statistical approaches and database similarity searches.

BRIEF DESCRIPTION OF THE DRAWINGS

The foregoing and other objects, aspects and advantages will be better understood from the following detailed description of a preferred embodiment of the invention with reference to the drawings, in which:

FIG. 4(a) provides Table 1 which describes the seventeen genomes studied in the inventors' experiments using the present invention;

FIG. 4(b) provides Table 2 which displays results generated in experiments using the present invention;

DETAILED DESCRIPTION OF PREFERRED EMBODIMENTS OF THE INVENTION

Figure 1:
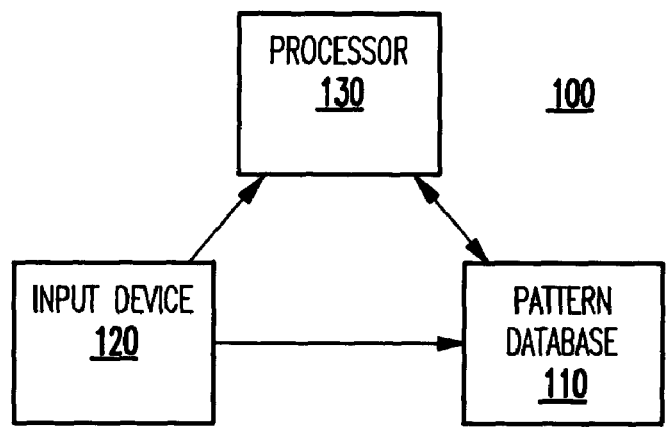
FIG. 1 illustrates a system 100 for identifying genes according to the present invention.

Referring now to the drawings, FIG. 1 illustrates an inventive system 100 for identifying genes according to the present invention.

As shown in FIG. 1, the inventive system 100 includes a pattern database 110 which includes patterns of amino acids. The patterns may be provided to system 100 or, optionally, the patterns may be derived from a database(s) comprising one or more amino acid sequence or fragment of an amino acid sequence, or otherwise be made available to the inventive system 100. The system 100 also includes an input device 120 for inputting data (e.g., a given DNA sequence) and instructions, and a processor 130 for processing the DNA sequence and patterns to identify a putative gene.

Specifically, the processor 130 may process input data to determine open reading frames (ORFS) in the DNA sequence, generate an amino acid translation for each ORF, and identify matches of the patterns in the amino acid translation. Optionally, the processor 130 may be used to also derive a database of patterns to be used with the present invention, by processing, for example, a database comprising one or more amino acid sequence or amino acid sequence fragment (e.g., proteins and/or protein fragments) with a pattern discovery algorithm such as the Teiresias algorithm.

The inventive system 100 provides a new approach for tackling the gene identification problem. The approach employs a pattern database 110 (e.g., a database of patterns that may or may not cover all of the currently available sample of natural protein sequence space) to determine gene candidates among the ORFs that can be identified in a given DNA strand. Further, the inventive system 100 combines the best characteristics from each of the above-mentioned schools of thought (e.g., statistical methods and similarity-based methods). In addition, the inventive system 100 may associate the patterns in the pattern database 110 with appropriately computed weights which leads to further improvements in the gene identification ability.

The concept of the pattern database was introduced in a number of publications on the "IBM Bio-Dictionary(TM)" work including Rigoutsos, I., Floratos, I., et al., (1999) "Dictionary Building vis Unsupervised Hierarchical Motif Discovery" Journal of Proteins: Structure, Function and Genetics, 37 (2) (hereinafter "Article 1"); Rigoutsos, I., Floratos, I., et al., (2000) "The Emergence of Pattern Discovery Techniques in Computational Biology", *Journal of Metabolic Engineering,* 2(3), 159-177 (hereinafter "Article 2"); and Rigoutsos, I., Gao, Y., et al., (1999), "Building Dictionaries of 1D and 3D Motifs by Mining the Unaligned ID Sequences of 17 Archaeal and Bacterial Genomes", *Proc. ISMB* '99 (hereinafter "Article 3), which are all incorporated herein by reference.

The pattern database 110 may be created by using, for example, the Teiresias algorithm, which is explained in Rigoutsos, I., and Floratos, A., (1998) "Combinatorial Pattern Discovery in Biological Sequences: The Teiresias Algorithm", *Bioinformatics,* 14(1):55-67 and Rigoutsos, I., and Floratos, A., (1998), "Motif Discovery Without Alignment or Enumeration", *Proc. 2$^{nd}$ ACM International Conference on Computational Molecular Biology* (RECOMB '98), which are incorporated herein by reference.

For instance, if $\Sigma$ denotes the alphabet of all 20 amino acids, when processing an input dataset containing a collection of strings from $\Sigma^+$ with the Teiresias algorithm, one can succinctly capture the patterns that can be discovered with the regular expression $\Lambda(\Lambda \cup \{"."\})^*\Lambda$ where $\Lambda=(\Sigma \cup \Sigma\Sigma^*\Sigma])$. In this expression, '.' is a "don't care" character which can be replaced by any character in $\Sigma$. That is, the generated patterns can either be a single alphabet symbol, or strings that begin and end with a symbol or a bracket with two or more characters, and contain an arbitrary combination of zero or more residues, brackets with at least two alphabet characters, and don't care characters. A bracket is meant to denote a "one of" choice. In other words, for example, [CPM] denotes exactly one of C, P or M. Also, a bracket can have a minimum of 2 (two) alphabet characters but obviously not more than $|\Sigma|-1$.

A pattern t is called an <L,W> pattern (with $L \leq W$) if every substring of t of length W comprises L or more non-don't care positions. The smallest length of an <L,W> pattern is obviously equal to L whereas its maximum length is unbounded. Any given choice for the parameters L and W has a direct bearing on the degree of remaining similarity among the instances of the sequence fragments that the pattern captures. Thus, the smaller the value of the ratio L/W, the lower the degree of local similarity. Associated with each pattern t is its support which is denoted by K and represents the minimum number of instances of a pattern t in the input database from which it was derived.

The patterns of amino acids stored in the pattern database 110 are commonly referred to simply as patterns. As noted above, the patterns may completely describe and account for the currently known sequence space of natural proteins at the amino-acid level. However, this is not a necessity for this algorithm to operate. The patterns may be derived, for example, by processing a large public database (e.g., GenPept or SwissProt) of proteins and protein fragments using the Teiresias algorithm and discovering patterns that occur a certain number of times (e.g., discovering all <6,15> patterns that occur 2 or more times, i.e. L=6, W=15, and K=2). Alternatively, the patterns may be provided to the algorithm through other means, e.g., through access to an existing collection of patterns such as those contained in the PROSITE database. The availability of such a collection of patterns permits a user to effectively and successfully tackle a number of tasks including, for example, similarity searching (e.g., see Floratos, A., Rigoutsos, I., et al., (1999) "Sequence Homology Detection Through Large Scale Pattern Discovery", *Proc. RECOMB* '99), functional annotation (e.g., see Article 3), phylogenetic domain analysis (e.g., see Article 2), as well as gene identification.

For example, in Article 1, the inventors described how to compute a pattern database from the GenPept release from Feb. 10, 1999 that contains ~387,000 sequences with a grand total of ~120M amino acids. The computation gave rise to a pattern database 110 that comprised ~26M patterns and which accounted for (i.e. covered) 98.12% of the amino acid positions in the processed input.

As explained above, the pattern database 110 may substitute a given sequence database of proteins and fragments by a collection of patterns (i.e. regular expressions) that represents combinations (e.g., patterns) of amino acids that appear two or more times in the processed input.

Therefore, the inventive system 100 is able to successfully tackle the problems sought by researchers for several reasons. For instance, the pattern database 110 could be extracted from a large and diverse collection of proteins and protein fragments which are readily available, given the currently large number of completed and ongoing genome sequencing projects which contribute to the public databases (e.g., see Article 2). In other words, the invention may assume that a set of patterns has been made available somehow and simply uses these patterns.

Referring again to FIG. 1, the inventive system also includes an input device 120. The input device 120 (e.g., a keyboard) may be used, for example, to input data (e.g., data generated by the user, or downloaded from another database such as a public database) to the inventive system 100, and for inputting instructions for processing the input dataset by the processor 130. For example, the input device 120 may be used to input a DNA sequence.

The inventive system 100 may also include a memory device (e.g., RAM, ROM, etc.) which stores input data and instructions for processing such data. For example, such data may be downloaded from another database via the World Wide Web (e.g., Internet) into the memory device. For example, a DNA sequence to be studied for the presence of genes in it may be stored in the memory device (e.g., RAM, ROM, etc.) in the inventive system 100. Alternatively, data (e.g., a dataset) may be downloaded to the inventive system 100 directly from another database, for example, over the World Wide Web (e.g., Internet) and processed by the inventive system 100 without being permanently stored therein.

As shown in FIG. 1, the inventive system 100 also includes a processor 130 (e.g., a microprocessor) which may be used to process the data which is input into the inventive system 100. The processor 130, may translate an input DNA sequence into an amino acid translation. Further, the processor 130 may perform a process (e.g., a pattern matching process) in order to match the patterns of amino acids stored in the pattern database 110 with the amino acid translation from the input DNA sequence.

In short, the processor 130 may process the input DNA sequence to be studied by determining all possible open reading frames (ORFs) in the DNA sequence. An ORF may include, for example, the DNA sequence between a start codon and a stop codon. For example, the processor 130 may compute all possible ORFs in each of the reading frames (e.g, three reading frames), and both for the forward and reverse strands of the given DNA sequence. The number of truly coding regions will be a proper subset of this collection of ORFs.

For each ORF, the processor 130 may generate an amino acid translation. If the ORF under consideration is indeed a coding sequence, then the instances of one or more of the patterns from the pattern database 110 should be identifiable in the ORF's translation, and vice versa. If the number of patterns whose located instances exceeds a predetermined threshold, the ORF may be reported as a putative gene. Further, the higher the number of patterns that can be found in a given ORF and the more evenly their instances are distributed over the ORF's translation, the more likely it is that the ORF under consideration is a coding sequence.

To improve the efficiency of the inventive system 100 (e.g., to improve the gene-identifying capabilities of the inventive system 100) an optional weighting scheme may be included. In other words, in addition to the number of patterns that can be located within the translation of an ORF, the very nature of these patterns carries weight when deciding whether the ORF is indeed a coding one. In general, any two patterns that will match an amino acid translation will affect this decision differently. By summing up the scores of the patterns matching an ORF, a quality measure can be determined that will allow the ORF to be characterized as a putative gene, or otherwise.

The processor 130 may, therefore, optionally weight the patterns in the pattern database 110. For instance, where $T = \{t_1 t_2 \ldots, t_n\}$ is the complete collection of patterns in the pattern database 110, if a putative protein s is coded for by some ORF from a given DNA sequence, and l is the length of s, it could be said that a pattern matches at position j of the amino acid sequence s if an instance of the pattern can be found beginning at the j-th location of s.

Further, letting Tsj denote the set of patterns that match beginning at position j of s, letting $T'_{sj}$ denote the set $T/T_{sj}$, letting $T_s = \{t_{v1}, t_{v2}, \ldots t_{vm}\}$ denote the concatenated list of $T_{sj}$'s for all j ($1 \leq j \geq 1$), it can be seen that $T'_{sj}$'s for different j's can contain the same pattern, thus $T_s$ is in general a multiset.

The inventive system may, therefore, determine a coding quality measure for an ORF under consideration based, in part, on the probability, $p_i$, that pattern $t_i$ matches an actual amino acid sequence at a fixed location, and the probability, $q_i$, that $t_i$ matches the amino acid translation of a non-coding ORF at a fixed location.

For instance, letting $w_i = \log p_i - \log q_i$ where $w_i$ is the weight associated with pattern $t_i$, and considering the sum of weights of the patterns matching anywhere in the translation s of an ORF as the measure $W_s$ that is characteristic of the coding quality of the ORF under consideration, in many cases the following equation can be used to express the coding quality measure of an ORF:

$$W_s = \sum i \stackrel{m}{=} 1 w_{v_i} = \sum i \stackrel{m}{=} 1 (\log p_{v_i} - \log q_{v_i}) = \log R''^3_s$$

where $R''_s$ is an approximation of the relative likelihood that two candidate ORFs are coding.

Further, at times, a situation may be encountered where multiple start codons match the same stop codon so that the appropriate start/stop pair must be chosen. A straightforward solution may involve picking the start codon which will result in the highest value for the coding quality measure. However, selecting the start codon in such a way will not necessarily result in the longest ORF because patterns can also have negative associated weights.

On a related note, ATG is the most frequently used start codon but not the only one. It is thus conceivable that the different start codons be treated in a non-uniform manner. For example, if $\{c_1, c_2, \ldots, c_k\}$ denotes the set of possible start codons, and $f_i$ is the probability that $c_i$ is the start codon of a randomly chosen coding region, and if $f'_i$ is the probability that $c_i$ is observed in non-coding regions, and $g_i$ is given as log $f_i - \log f'_i$, the term $W_s + g$ may be used (instead of $W_s$) as the measure of coding quality for the amino acid translation s of an ORF that is initiated by the start codon $c_i$.

The inventive system 100 may, therefore, optionally utilize the values for $p_i$'s and $q_i$'s to compute the coding quality measure. One way to compute these $p_i$'s and $q_i$'s is to compute them with the help of known actual genes and non-coding ORFs. Further, the values of $f_i$'s and $f'_i$'s can also be obtained from the same training set.

But these values may also be obtained in the absence of a training set. For example, for $p_i$ values, the probabilities computed with the help of the protein database from which the pattern database is derived can be used. Alternatively, the values can be computed using, for example, very long ORFs instead of actual coding regions. In addition, to obtain $q_i$ values, non-ORF regions can be used, or the values may be obtained by estimating the probability of random occurrence based on an appropriately chosen amino acid bias.

When each ORF has been associated with its coding quality measure, the inventive system 100 may determine which ORFs correspond to putative genes by appropriately setting a threshold value. Such a threshold value may be input by a user using the input device 120 or may, for example be stored in a memory device accessible by the processor 130. The higher the value of the measure for a given ORF the more likely it is that it is a coding one.

Further, the inventive system 100 may use the processor 130 to identify matches of the patterns from the pattern database in the amino acid translation from an input DNA sequence by using, for example, a nested loop or other method. Alternatively, a predetermined algorithm may be used to identify matches of the patterns in the amino acid translations.

For instance, using a predetermined algorithm, the processor 130 in the inventive system 100 may compare the patterns in the pattern database 110 with the amino acid translations of a large number of ORFs for each complete genome. This operation may be carried out as efficiently as possible so as to reduce computing time. The inventive system 100 may, therefore, include an algorithm (e.g., an algorithm stored in a memory device accessible by the processor 130) for performing such comparison.

Therefore, in summary, the processor 130 in the inventive system 100 may determine possible open reading frames (ORFs) in the DNA sequence, generate an amino acid translation for each ORF, and identify matches of the patterns in the amino acid translation. Further, the processor 130 may output the results of such computations to a database (e.g., a memory device such as RAM, ROM etc.). Further, the results may also be output to a display device (e.g, video display device) or printer for analysis by a user.

Figure 2:
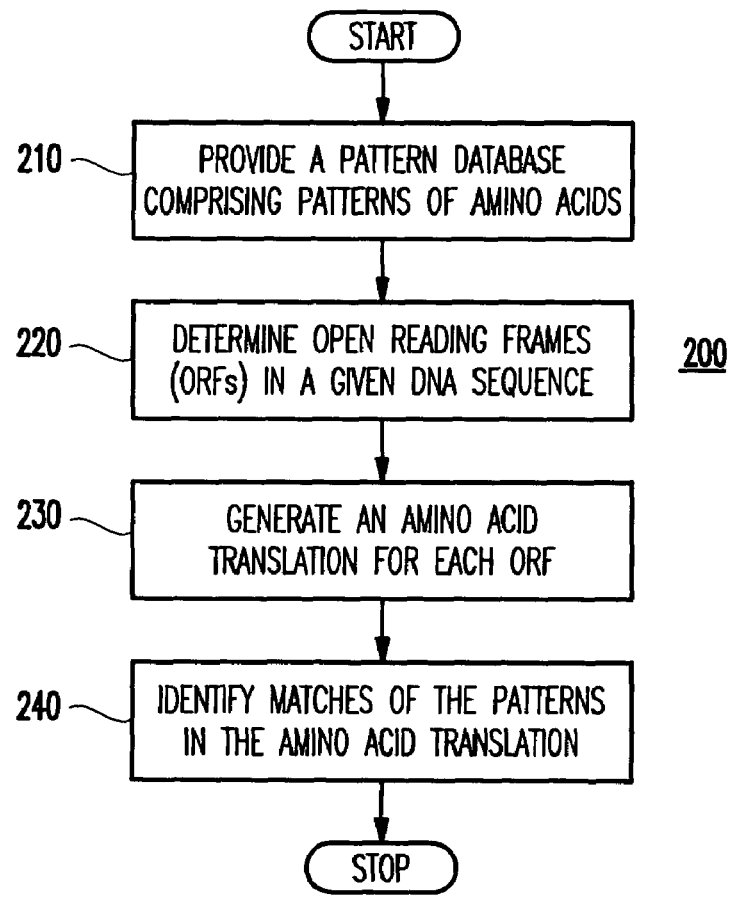
FIG. 2 is a flowchart illustrating a method 200 of identifying genes according to the present invention.

Referring again to the figures, FIG. 2 is a flowchart illustrating an inventive method 200 for identifying genes according to the present invention. As shown in FIG. 2, the inventive method 200 includes providing (210) a pattern database comprising patterns of amino acids. For instance, the pattern database may be derived from a database of one or more amino acid sequence or amino acid sequence fragment (e.g., proteins or protein fragments). The inventive method 200 also includes computing (220) all possible open reading frames (ORFs) in a DNA sequence, generating (230) an amino acid translation for each ORF, and identifying (240) matches of patterns from the pattern database in the ORF's amino acid translation.

Figure 3:
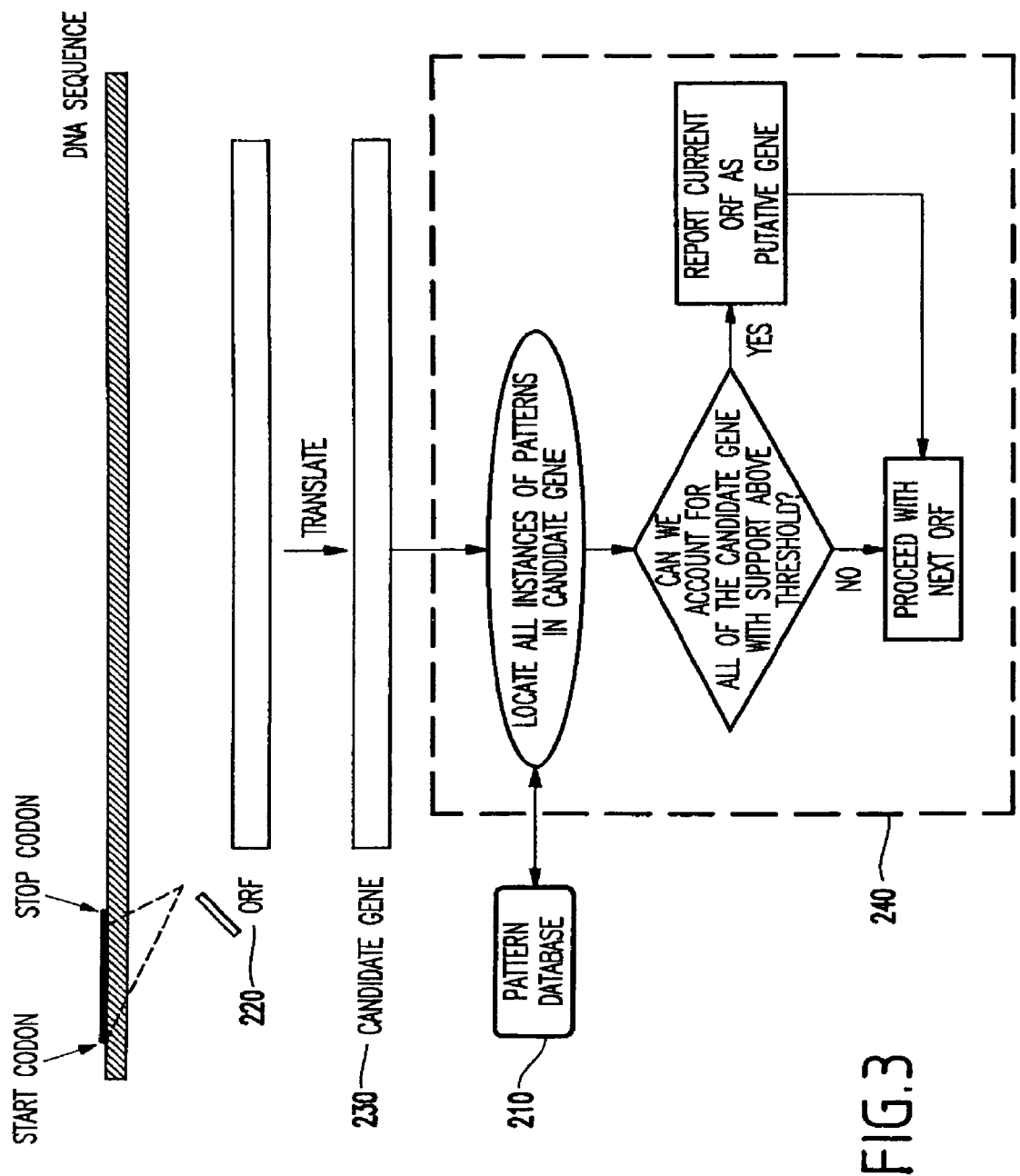
FIG. 3 illustrates an exemplary embodiment of the inventive method 200 according to the present invention.

The inventive method 200 may be more clearly understood by referring to FIG. 3 which illustrates an example of the inventive method 200 as it is used to identify genes in a given DNA sequence. As shown in FIG. 3, the inventive method 200 provides (210) a pattern database (e.g., from a database (e.g., a public database) of amino acids or amino acid fragments (e.g., proteins and/or protein fragments)). The inventive method 200 also computes (220) possible open reading frames (ORFs) in a DNA sequence, and generates (230) an amino acid translation (e.g., a candidate gene) for each ORF.

The inventive method 200 may, thus, identify (240) matches of patterns from the pattern database in the amino acid translation, for example, by locating instances (e.g., matches) of patterns from the pattern database in the candidate gene and determining if support goes above the given threshold value. If yes, the ORF may be reported as a putative gene, and if not, the inventive method 100 proceeds with the next ORF.

Experiments and Results

Experiments conducted by the inventors have confirmed the efficacy and efficiency of the present invention. For example, the inventors have applied the present invention and gene-finding algorithm to several archaeal and bacterial genomes.

In the experiments, the inventors generated a pattern database with the help of the Teiresias algorithm. Specifically, an instance of the pattern database known as the IBM Bio-Dictionary was computed for the Nov. 15, 1999 release of the GenPept database which contained 448,290 proteins and protein fragments corresponding to a total of 122,609,801 amino acids (this was the same process explained in Article 1). The pattern database generated by the inventors from the Nov. 15, 1999 release of GenPept contained 31,184,670 patterns (e.g., small sequences commonly referred to as "seqlets"). These patterns accounted for 98.10% of the amino acids in the processed database.

It should be pointed out that the GenPept release used to build the pattern database chronologically preceded the releases of several of the test genomes that the inventors have processed and on which the inventors ran their experiments. This was an intentional choice by the inventors and was meant to demonstrate the present invention's extrapolation capability.

In their experiments, the inventors used the present invention to process seventeen (17) complete genomes. Of these genomes, four were archaeal (*A. fulgidus, M jannaschii, M thermoautotrophicum, P. abyssi*) whereas the remaining thirteen were bacterial. Table 1 in FIG. 4(*a*) shows the list of the genomes as well as their lengths in nucleotides, the numbers of all identifiable ORFs that are longer than 60 nucleotides, and the numbers of annotated coding regions from each genome that have been included in the public databases. In FIG. 4(*a*), it can be seen that the number of coding regions is roughly ⅟1000-th of the length of the genome. It is also very likely that these genomes contain coding regions that have not yet been reported. Also, it must be remembered that these annotated coding regions are in reality putative and have been annotated by scientists typically in the absence of wet laboratory experiments.

The inventors first carried out experiments using pattern weights that were computed separately from the reported coding regions of each genome as listed in the public databases.

Table 2 in FIG. 4(*b*) shows the results of the experiments using the present invention (e.g., using the inventive gene finding algorithm). Here, the open reading frames that occupy the top (a) 1.0×#CDS and (b) 1.1×#CDS positions when sorted in decreasing value of coding quality as potential coding regions are reported. In FIG. 4(*b*), #CDS is the number of annotated coding regions in the databases (see last column of Table 1 in FIG. 4(*a*)). It should be noted that the number of not-previously-predicted annotated genes is equal to that of reported additional putative genes in the case "a" as shown in the left hand column of the table.

The 'Annotated' column in Table 2 (FIG. 4(*b*)) shows the numbers of correctly predicted ORFs. In this case, ORFs which were reported as putative genes overlap with regions that have been designated as coding in the public databases. This result is also shown as a percentage of the genes that have already been reported in the genomic database entry for the respective genome (see, for example, the last column of Table 1 in FIG. 4(*a*)).

The 'Additional' column shows the number of ORFs that the present invention reported as putative genes but for which there was no database entry characterizing them as such. The 'Hit' column shows how many of these "additional putative genes" have substantial similarity with proteins contained in the Jan. 15, 2001 release of SwissProt/TrEMBL, which are found by FASTA with default options and reported to have E(.) values that are not larger than 1.0e-5. The 'Score' column shows the lowest value of the coding quality measure for the ORFs which were reported as putative genes.

As shown in Table 2 (FIG. 4(*b*)), the present invention can achieve very high prediction rates. In particular, when the top 1.1×#CDS positions are considered (e.g., case "b" above as shown in the right hand column of Table 2), the prediction ratios, (i.e. the rates of predicted ORFs among annotated coding regions) exceed the 94% mark for all of the genomes examined by the inventors. As a matter of fact, and with the exception of the *E. coli* and *Synechocystis sp.* genomes, the inventors' prediction rates exceed the 98% mark. For many of these genomes, additional putative genes (listed in the 'Additional' column) that almost invariably share similarities with proteins from SwissProt/TrEMBL according to FASTA, are reported. These additional putative genes are likely to be coding with high probability. The coding quality measures that the present invention attributed to these ORFs is high enough to warrant laboratory experiments which can verify that the ORFs are indeed coding. It is notable that the present invention here achieved perfect prediction in the case of *B. burgdorferi*. Given that the inventors made no use of information regarding promoter regions, terminators or enhancers, the results achieved by the present invention were very encouraging.

It is worth stressing the fact that these high prediction rates were achieved by using the same universal set of pattern weights on all genomes. This is in marked contrast with methods that are based on statistical techniques, such as HMMs, where the user computes and uses genome-specific parameters, and is indicative of the potential of the present invention.

In summary, the present invention provides a new system and method for solving the gene identification problem. The invention relies in part on a straightforward idea and as the reported experimental results demonstrate, it can predict genes very accurately. So as to further demonstrate the capabilities of the invention, the inventors intentionally relied upon a pattern database that was built from a November 1999 release of GenPept and applied it to genomes whose ORFs were only in part included in GenPept or not included at all. It is easy to see how repeating the gene discovery process with a pattern database that is computed from a more recent release of a public database such as GenePept would further improve the quality of the inventors' experimental results.

In addition, the inventors could potentially augment the present invention by associating each of the patterns in the pattern database with manually-derived or automatically-derived weights.

Further, it should be noted that in addition to correctly finding those of the ORFs that have already been reported in the public databases as putative genes, the present invention determines additional candidate genes in almost every single one of the genomes on which the inventors ran experiments. The inventors used FASTA to determine similarities between the additional candidate genes and the entries currently in SwissProt/TrEMBL and, in fact, such similarities were identified for many of these genes (see Table 2 in FIG. 4(b)).

Figure 5:
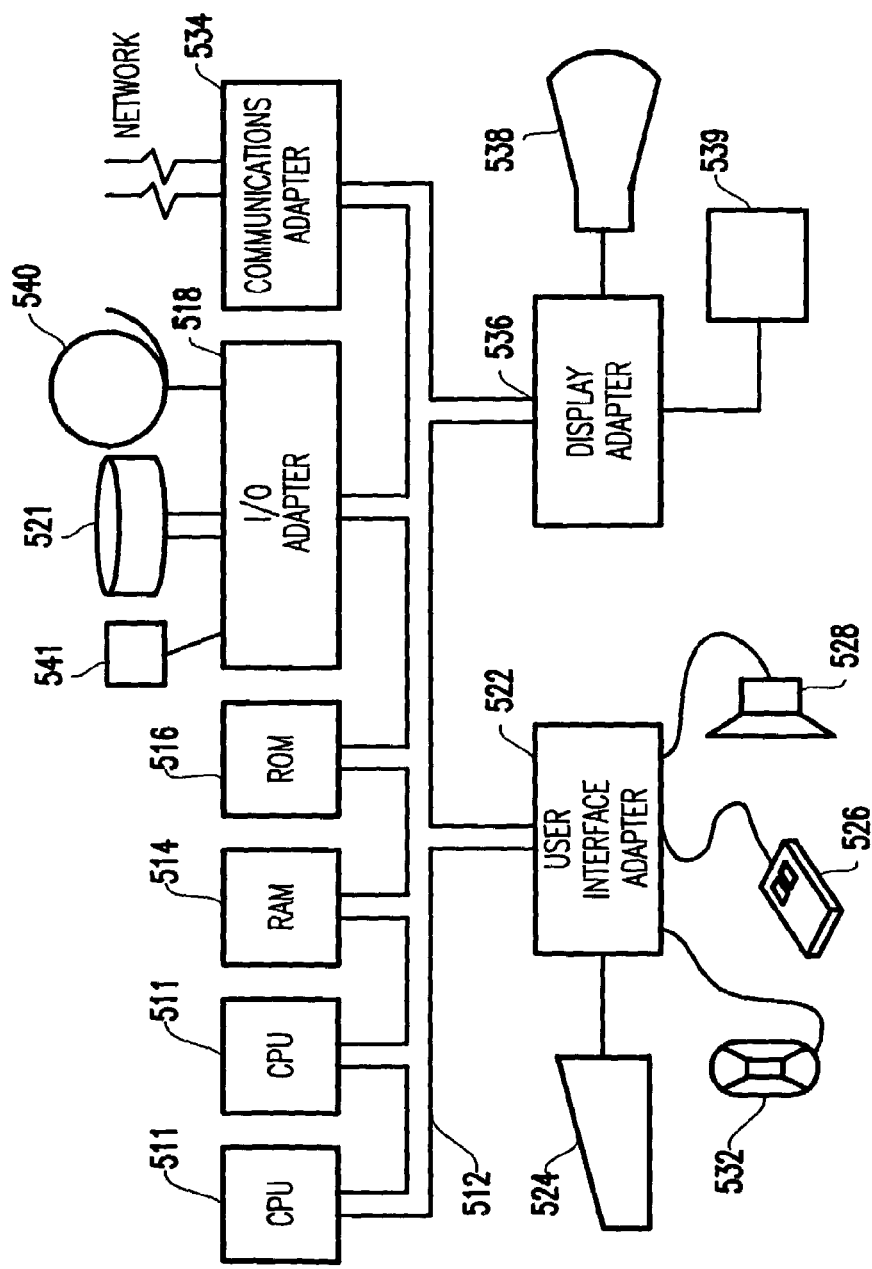
FIG. 5 illustrates a typical hardware configuration 500 which may be used for implementing the present invention.

Referring now to FIG. 5, system 500 illustrates a typical hardware configuration which may be used for implementing the inventive system and method for identifying genes. The configuration has preferably at least one processor or central processing unit (CPU) 511. The CPUs 511 are interconnected via a system bus 512 to a random access memory (RAM) 514, read-only memory (ROM) 516, input/output (I/O) adapter 518 (for connecting peripheral devices such as disk units 521 and tape drives 540 to the bus 512), user interface adapter 522 (for connecting a keyboard 524, mouse 526, speaker 528, microphone 532, and/or other user interface device to the bus 512), a communication adapter 534 for connecting an information handling system to a data processing network, the Internet, and Intranet, a personal area network (PAN), etc., and a display adapter 536 for connecting the bus 512 to a display device 538 and/or printer 539. Further, an automated reader/scanner 541 may be included. Such readers/scanners are commercially available from many sources.

In addition to the system described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, including signal-bearing media tangibly embodying a program of machine-readable instructions executable by a digital data processor to perform the inventive method.

Such a method may be implemented, for example, by operating the CPU 511 to execute a sequence of machine-readable instructions. These instructions may reside in various types of signal bearing media.

Thus, this aspect of the present invention is directed to a programmed product, comprising signal-bearing media tangibly embodying a program of machine-readable instructions executable by a digital data processor incorporating the CPU 511 and hardware above, to perform the method of the invention.

Figure 6:
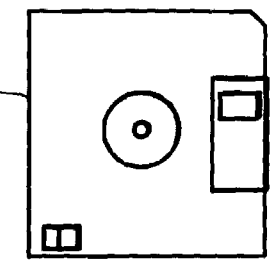
FIG. 6 illustrates a signal bearing medium 600 for performing a method of identifying genes according to the present invention.

This signal-bearing media may include, for example, a RAM contained within the CPU 511, as represented by the fast-access storage for example. Alternatively, the instructions may be contained in another signal-bearing media, such as a magnetic data storage diskette 600 (FIG. 6), directly or indirectly accessible by the CPU 511.

Whether contained in the computer server/CPU 511, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, complied from a language such as "C," etc.

With its unique and novel features, the present invention provides a novel system and method which accurately and efficiently identifies genes. The present invention may be considered to combine the best characteristics of statistical approaches and database similarity searches.

While the invention has been described in terms of preferred embodiments, those skilled in the art will recognize that the invention can be practiced with modification within the spirit and scope of the appended claims. For example, instead of a database of patterns of amino acids, alternatively a user could employ a database of patterns based on nucleotides (e.g., generated or provided) and match the patterns of the database in an open reading frame (ORF) so as to eliminate the need to translate the candidate ORF.

What is claimed is:

1. A system for identifying genes, comprising:
a pattern database comprising patterns of amino acids;
an input device for inputting a genomic DNA sequence; and
a processor which is configured to:
translate an open reading frame (ORF) of said DNA sequence into an amino acid translation;
assign weights, $w_i$, to said patterns of amino acids, said weights being given by the equation $w_i = \log p_i - \log q_i$, where $p_i$ is a probability that a pattern matches an actual amino acid sequence at a fixed location, and $q_i$ is a probability that said pattern matches an amino acid translation of a non-coding ORF;
locate in said amino acid translation occurrences of said weighted patterns, and assign a coding quality measure for said ORF which is given by $$Ws = \sum_{i=1}^{m} w_i,$$

where m is the number of patterns which are located in said amino acid translation of said ORF; and
identify said open reading frame as including a putative gene if a value of said coding quality measure is greater than a predetermined threshold value.

2. The system according to claim 1, wherein said processor translates a plurality of open reading frames in said DNA sequence into amino acid translations, and locates in each amino acid translation occurrences of said patterns to determine whether each said plurality open reading frames includes a putative gene.

3. The system according to claim 2, wherein said patterns comprise biologically significant patterns of amino acids in amino acid sequences.

4. The system according to claim 1, wherein said processor identifies a match of a pattern from said pattern database in said amino acid translation.

5. The system according to claim 4, wherein said patterns are derived from a parent database comprising at least one amino acid sequence.

6. The system according to claim 4, wherein said patterns are derived from a parent database comprising at least one amino acid sequence fragment.

7. The system according to claim 4, wherein said patterns are derived by using a pattern discovery algorithm.

8. The system according to claim 4, wherein said patterns are derived by using the Teiresias algorithm.

9. The system according to claim 4, wherein said ORF comprises a portion of said DNA sequence between a start codon and a stop codon.

10. The system according to claim 4, wherein said processor reports said ORF as a putative gene when a predetermined number of pattern matches is identified in said amino acid translation.

11. The system according to claim 4, wherein each pattern is assigned a weight depending upon a relevance of said pattern in determining whether said ORF comprises a putative gene.

12. The system according to claim 4, wherein said processor is configured to select a start codon which results in a greatest value of said coding quality measure, in a case in which plural start codons match the same stop codon.

13. The system according to claim 4, wherein said match is identified using a predetermined pattern matching algorithm.

14. The system according to claim 4, further comprising:
a memory device for storing data and instructions to be executed by said processor.

15. The system according to claim 4, further comprising:
a display device for displaying an output from said processor.

16. A method of identifying genes, comprising:
providing a pattern database comprising patterns of amino acids;
determining an open reading frame (ORF) in a genomic DNA sequence;
generating an amino acid translation for said ORF;
assigning weights, $w_i$, to said patterns of amino acids, said weights being given by the equation $w_i = \log p_i - \log q_i$, where $p_i$ is a probability that a pattern matches an actual amino acid sequence at a fixed location, and $q_i$ is a probability that said pattern matches an amino acid translation of a non-coding ORF;
locating a match of said weighted patterns from said pattern database, in said amino acid translation and assigning a coding quality measure for said ORF which is given by $$Ws = \sum_{i=1}^{m} w_i,$$

where m is the number of patterns which are located in said amino acid translation of said ORF;
identifying said ORF as including a putative gene if a value of said coding quality measure is greater than a predetermined threshold value; and
displaying a result of said identifying said ORF as including a putative gene.

17. The method according to claim 16, wherein said pattern database is generated from a database comprising at least one amino acid sequence.

18. The method according to claim 16, wherein said pattern database is generated from a database comprising at least one amino acid sequence fragment.

19. The method according to claim 16, wherein said probability, $p_i$, is calculated based on a training set.

20. The method according to claim 19, wherein said probability, $q_i$, is calculated by computing a number of occurrences of a pattern in ORFs that are not identified as coding in said training set.

21. The method according to claim 16, further comprising:
displaying said match of said pattern in said amino acid translation.

22. The method according to claim 16, wherein said pattern database is generated using the Teiresias algorithm to derive said patterns from a parent database.

23. A programmable storage medium tangibly embodying a program of machine-readable instructions executable by a digital processing apparatus to perform a method for identifying genes, said method comprising:
providing a pattern database comprising patterns of amino acids;
determining an open reading frames (ORF) in a given genomic DNA sequence;
generating an amino acid translation for each ORF;
assigning weights, $w_i$, to said patterns of amino acids, said weights being given by the equation $w_i = \log p_i - \log q_i$, where $p_i$ is a probability that a pattern matches an actual amino acid sequence at a fixed location, and $q_i$ is a probability that said patter matches an amino acid translation of a non-coding ORF;
locating a match of said weighted patterns from said pattern database, in said amino acid translation and assigning a coding quality measure for said ORF which is given by $$Ws = \sum_{i=1}^{m} w_i,$$

where m is the number of patterns which are located in said amino acid translation of said ORF;
identifying said ORF as including a putative gene if a value of said coding quality measure is greater than a predetermined threshold value; and
displaying a result of said identifying said ORF as including a putative gene.

24. The system according to claim 3, wherein said processor determines for each pattern in said pattern database whether the pattern is present in said amino acid translation by locating instances of said patterns in said amino acid translation, until a sum of weights corresponding to all patterns with matches in said amino acid translation exceeds a predetermined threshold, at which point said processor identifies said ORF as a putative gene.

25. The system according to claim 1, further comprising:
a parent database comprising a plurality of amino acid sequences, said patterns in said pattern database being derived from said plurality of amino acid sequences by using a pattern discovery algorithm;
a memory device for storing data and instructions to be executed by said processor; and
a display device for displaying an output from said processor.

26. The system according to claim 25, wherein said open reading frame (ORF) comprises a portion of said DNA sequence between a start codon and a stop codon, wherein said processor identifies a match of a pattern from said pattern database in said amino acid translation by using a predetermined pattern matching algorithm, wherein each pattern is assigned a weight depending upon a relevance of said pattern in determining whether said ORF comprises a putative gene, and wherein said ORF is reported as a putative gene when either a predetermined number of pattern matches is identified in said amino acid translation, or a sum of weights corresponding to all patterns with matches in said amino acid translation exceeds a predetermined threshold.

27. The system according to claim 1, wherein said processor accesses said pattern database to retrieve said patterns from said pattern database.

28. The system according to claim 1, wherein said processor is electrically coupled to said input device and said pattern database.

29. A system for identifying genes, comprising:
an input device which inputs a genomic DNA sequence; and
a processor which is configured to:
    access a pattern database comprising a plurality of patterns of amino acids;
    translate an open reading frame (ORF) of said DNA sequence into an amino acid translation;
    assign weights, $w_i$, to said patterns of amino acids, said weights being given by the equation $w_i = \log p_i - \log q_i$, where $p_i$ is a probability that a pattern matches an actual amino acid sequence at a fixed location, and $q_i$ is a probability that said pattern matches an amino acid translation of a non-coding ORF;
    locate in said amino acid translation occurrences of said weighted patterns, and assign a coding quality measure for said ORF which is given by $Ws=$ $$Ws = \sum_{i=1}^{m} w_i,$$

where m is the number of patterns which are located in said amino acid translation of said ORF; and identify said open reading frame as including a putative gene if a value of said coding quality measure is greater than a predetermined threshold value.

30. A system for identifying genes, comprising:
an input device which inputs a query genomic DNA sequence;
a processor which is configured to:
    access a pattern database comprising a plurality of patterns of amino acids;
    translate an open reading frame (ORF) of said DNA sequence into an amino acid translation;
    assign weights, $w_i$, to said patterns of amino acids, said weights being given by the equation $w_i = \log p_i - \log q_i$, where $p_i$ is a probability that a pattern matches an actual amino acid sequence at a fixed location, and $q_i$ is a probability that said pattern matches an amino acid translation of a non-coding ORF;
    locate in said amino acid translation occurrences of said weighted patterns, and assign a coding quality measure for said ORF which is given by $$Ws = \sum_{i=1}^{m} w_i,$$

where m is the number of patterns which are located in said amino acid translation of said ORF; and identify said open reading frame as including a putative gene if a value of said coding quality measure is greater than a predetermined threshold value a display device for displaying an output of said processor, said output including an occurrence of said patterns in said amino acid translation, wherein said patterns comprises patterns derived using a Teiresias algorithm, wherein said open reading frame (ORF) comprises a portion of said DNA sequence between a start codon and a stop codon, and wherein said processor identifies a match of a pattern from said pattern database in said amino acid translation by using a predetermined pattern matching algorithm.

* * * * *